(12) United States Patent
Wright

(10) Patent No.: US 8,366,782 B2
(45) Date of Patent: Feb. 5, 2013

(54) MODULAR ORTHOPAEDIC IMPLANT SYSTEM WITH MULTI-USE STEMS

(75) Inventor: Abraham Paul Wright, Winona Lake, IN (US)

(73) Assignee: Depuy Products, Inc., Warsaw, IN (US)

( * ) Notice: Subject to any disclaimer, the term of this patent is extended or adjusted under 35 U.S.C. 154(b) by 1557 days.

(21) Appl. No.: 10/912,325

(22) Filed: Aug. 5, 2004

(65) Prior Publication Data

US 2006/0030945 A1    Feb. 9, 2006

(51) Int. Cl.
*A61F 2/38* (2006.01)
(52) U.S. Cl. ................................................ 623/20.15
(58) Field of Classification Search .... 623/20.14–20.16, 623/20.21, 20.32–20.36
See application file for complete search history.

(56) References Cited

U.S. PATENT DOCUMENTS

| | | | |
|---|---|---|---|
| 4,822,366 A * | 4/1989 | Bolesky | 623/20.15 |
| 5,061,271 A | 10/1991 | Van Zile | |
| 5,133,760 A | 7/1992 | Petersen et al. | |
| 5,182,921 A | 2/1993 | Yan | |
| 5,290,313 A | 3/1994 | Heldreth | |
| 5,556,433 A | 9/1996 | Gabriel et al. | |
| 5,593,449 A | 1/1997 | Roberson | |
| 5,683,472 A | 11/1997 | O'Neil et al. | |
| 5,782,920 A | 7/1998 | Colleran | |
| 5,782,921 A | 7/1998 | Colleran et al. | |
| 5,824,097 A | 10/1998 | Gabriel et al. | |
| 5,879,341 A | 3/1999 | Slamin | |
| 5,879,391 A | 3/1999 | Slamin | |
| 5,944,756 A | 8/1999 | Fischetti et al. | |
| 6,126,693 A | 10/2000 | O'Neil et al. | |
| 6,149,687 A | 11/2000 | Gray et al. | |
| 6,171,342 B1 | 1/2001 | O'Neil et al. | |
| 6,214,052 B1 | 4/2001 | Burkinshaw | |
| 6,284,001 B1 | 9/2001 | Knapp | |
| 6,423,096 B1 | 7/2002 | Musset et al. | |

(Continued)

FOREIGN PATENT DOCUMENTS

| | | |
|---|---|---|
| EP | 0457222 A1 | 11/1991 |
| EP | 0947181 | 10/1999 |

(Continued)

OTHER PUBLICATIONS

De Puy Orthopaedics, Inc., P.F.C.® Sigma Knee System with Rotating Platform Technical Monograph, 3M0800, 0611-29-050, 1999, DePuy Orthopaedics, Inc. 700 Orthopaedic Drive, Warsaw, IN 46580, USA.

(Continued)

*Primary Examiner* — Alvin Stewart
*Assistant Examiner* — David Comstock

(57) ABSTRACT

A knee implant system includes a femoral adapter. The femoral adapter has a threaded bore so that a stem extension can be threaded onto the proximal end of the adapter. The same stem extension can be threaded onto the distal end of the tibial tray so that the number of stem extensions required in the system is reduced. The femoral adapter has a tapered exterior surface so that a metaphyseal sleeve can be frictionally connected to the femoral adapter. The metaphyseal sleeve has a threaded bore so that the same type of stem extension can be threaded onto the metaphyseal sleeve. The system can include a group of adapters to give the surgeon the option of selecting the appropriate valgus angle and anterior-posterior position of the stem extension.

15 Claims, 14 Drawing Sheets

U.S. PATENT DOCUMENTS

| | | |
|---|---|---|
| 6,436,149 B1 | 8/2002 | Rincoe |
| 6,443,991 B1 | 9/2002 | Running |
| 6,613,092 B1 | 9/2003 | Kana et al. |
| 6,727,723 B2 | 4/2004 | Shimizu et al. |
| 6,953,479 B2 | 10/2005 | Carson et al. |
| 2003/0014120 A1 | 1/2003 | Carson et al. |
| 2005/0107883 A1 | 5/2005 | Goodfried et al. |
| 2006/0142867 A1 | 6/2006 | Metzger et al. |
| 2009/0088862 A1 | 4/2009 | Thomas |

FOREIGN PATENT DOCUMENTS

| | | |
|---|---|---|
| EP | 1623686 | 2/2006 |
| FR | 2733411 A1 * | 10/1996 |
| WO | 91/18563 A1 | 12/1991 |
| WO | 03/065939 A1 | 8/2003 |
| WO | 2003065939 | 8/2003 |
| WO | 2007053905 | 5/2007 |

OTHER PUBLICATIONS

DePuy Orthopaedics, Inc., LCS® Complete™ Mobile-Bearing Knee System, 2001, DePuy Orthopaedics, Inc., 700 Orthopaedic Drive, Warsaw, IN 46580, USA.

European Search Report for European Patent Application No. 08165095.4-2310, Dec. 9, 2008, 8 pages.

Japanese Search Report for Corresponding Japanese Patent Application No. 2005-226873, Jul. 13, 2010, 2 pages.

European Search Report for Corresponding EPO Patent Application No. 05254634.8-2310/1623686 Dated Feb. 24, 2011, 10 Pages.

European Search Report for Corresponding EPO Application No. 05254634.8-2310/1623686 Dated Nov. 8, 2010, 6 pages.

\* cited by examiner

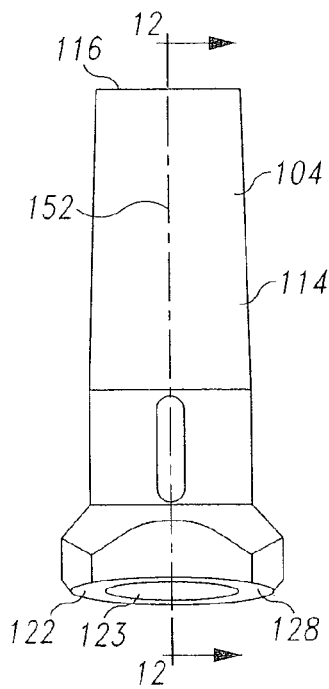
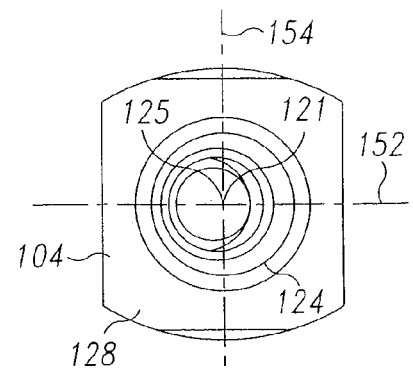
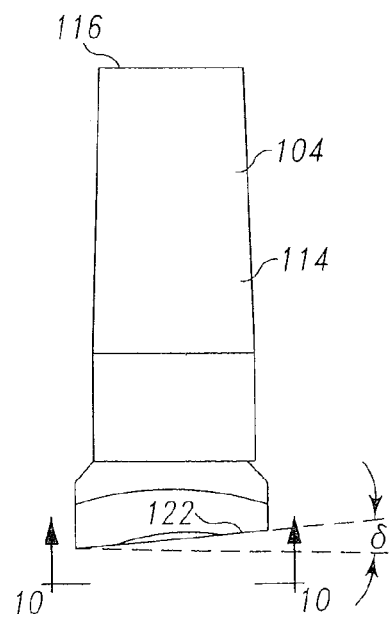
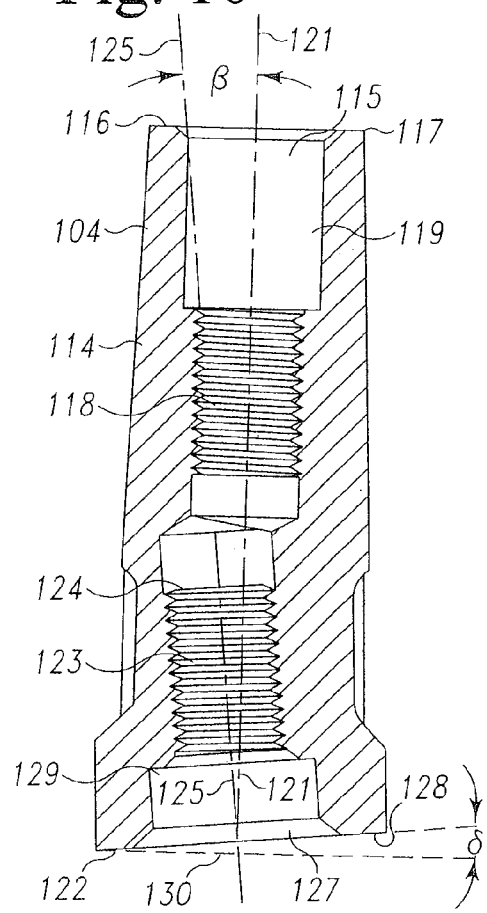
Fig. 9
Fig. 10
Fig. 11
Fig. 12

US 8,366,782 B2

MODULAR ORTHOPAEDIC IMPLANT SYSTEM WITH MULTI-USE STEMS

BACKGROUND OF THE INVENTION

The present invention relates generally to prosthetic joints and, more particularly, to modular orthopaedic knee implant systems.

The knee joint basically consists of the bone interface of the distal end of the femur and the proximal end of the tibia. Appearing to cover or at least partially protect this interface is the patella which is a sesamoid bone within the tendon of the long muscle (quadriceps) on the front of the thigh. This tendon inserts into the tibial tuberosity and the posterior surface of the patella is smooth and glides over the femur.

The femur is configured with two knob-like processes (the medial condyle and the lateral condyle) which are substantially smooth and which articulate with the medial plateau and the lateral plateau of the tibia, respectively. The plateaus of the tibia are substantially smooth and slightly cupped thereby providing a slight receptacle for receipt of the femoral condyles.

When the knee joint is damaged whether as a result of accident or illness, a prosthetic replacement of the damaged joint may be necessary to relieve pain and to restore normal use to the joint. Typically, the entire knee joint is replaced by means of a surgical procedure which involves removal of the surfaces of the corresponding damaged bones and replacement of these surfaces with prosthetic implants. This replacement of a native joint with a prosthetic joint is referred to as primary total-joint arthroplasty.

On occasion, the primary joint prosthesis fails. Failure can result from many causes, including wear, aseptic loosening, osteolysis, ligamentous instability, arthrofibrosis and patellofemoral complications. On such failure, a revision procedure may be necessary. In a revision, the primary joint prosthesis is removed and replaced with components of a revision joint system.

Implant systems for both primary and revision applications are available from a variety of manufacturers, including DePuy Orthopaedics, Inc. of Warsaw, Ind. DePuy and others offer several different systems for both primary and revision applications. For example, for the knee joint, DePuy Orthopaedics offers the P.F.C. SIGMA® Knee System, the LCS® Total Knee System and the S-ROM Modular Total Knee System. Each of these orthopaedic knee systems includes several components, some appropriate for use in primary knee arthroplasty and some appropriate for use in revision surgery.

An example of the existing DePuy P.F.C.SIGMA Knee System is illustrated in FIGS. 1-4. As shown in FIG. 1, a typical DePuy P.F.C. SIGMA modular orthopaedic knee implant system 8 includes a modular femoral implant 10 and a modular tibial implant 11. The modular femoral implant 10 includes a distal femoral component 12, an elongate femoral stem member 14, a bolt 16 and a femoral stem collar 18. The modular tibial implant 11 includes a tibial tray 13, a tibial insert 15 and an elongate tibial stem extension 17.

The modular femoral component 12 includes two spaced condylar portions 20, 22 with articulating surfaces 24, 26 to engage articulating surfaces 23, 25 of the tibial insert 15. As shown in FIGS. 2-3, on the proximal side of the femoral component 12, the two condylar portions 20, 22 are connected by an intercondylar box or boss 28. The intercondylar box or boss 28 has a pair of substantially vertical side walls 30, 32 that are connected by a top or superior seating or mounting platform 34. The boss mounting platform 34 is generally planar, and has an opening 36 (see FIG. 4) that extends through the boss to define an open channel. The bolt 16 extends through the channel from the distal side of the femoral component and through the opening 36 to be connected to a female threaded opening in the femoral stem 14. For clarity, the bolt's external threads are not shown on the drawings, but it should be understood that the proximal end of the bolt 16 is threaded.

The femoral stem collar 18 has a male portion 37 (FIG. 4) for connection to a distal female threaded end of the stem member 14. A retaining ring is used to hold the components 14, 37 together. Thus, the femoral stem member 14, stem collar 18 and femoral component 12 can be assembled to secure the stem member 14 to the femoral component 12. With this design, a variety of styles and sizes of stem members and femoral components can be assembled to best suit the patient's anatomy and joint conditions. For example, an implant kit could include a set of different sizes of stem members with outer surfaces adapted for cemented implantation as well as with fluted outer surfaces.

As shown in FIG. 3, when assembled, the femoral stem member 14 is typically angled in a medial direction. The angle is labeled in FIG. 3 as $\alpha$. The angle $\alpha$ is between the axis 40 of the femoral stem member 14 and a line 41 perpendicular to the plane 42 of the seating or mounting platform 34 of the intercondylar boss or box 28. The line 41 is also generally co-linear with the central longitudinal axis of the tibial stem extension 17. The angle $\alpha$ corresponds with the valgus angle when the implant assembly is implanted; the valgus angle is defined as the angle between the center line of the femur and the vertical axis connecting the distal femur and the center of the femoral head; the center line of the femur will correspond with the axis 40 of the stem member 14, and the vertical axis connecting the distal femur and the center of the femoral head will correspond with the line 41.

In the illustrated prior art modular assembly, the angle $\alpha$ is set by the structure of the femoral stem collar 18. The femoral stem collar has a superior side or surface 33 lying in a plane and an inferior side or surface 35 lying in a plane that is not parallel to the plane of the superior side or surface 33. The inferior surface 35 of the collar 18 is angled, defining an obtuse angle ($90°+\alpha$) with the axis 40 of the stem.

For the femoral side, a typical existing implant kit for DePuy's P.F.C. SIGMA Knee System includes: four sizes of femoral stem members 14 for use in cemented applications, with diameters of 13 mm and 15 mm and lengths of 90 mm and 130 mm; sixteen sizes of fluted femoral stem members 14 for non-cemented use, with diameters of 10 mm, 12 mm, 14, mm, 16 mm, 18 mm, 20 mm, 22 mm and 24 mm and lengths of 125 mm and 175 mm in each diameter; two bolts, a standard bolt and one providing a 2 mm anterior-posterior offset; and two stem collars 18 providing angles of 5° and 7° for the angle $\alpha$, although angles $\alpha$ may be in a typical range of 5-9°. A variety of sizes of distal femoral components 12 are also included in the typical commercial kit. With this variety of modular components, the surgeon can customize the femoral side of the prosthesis to best fit the needs of the individual patient.

Although not shown in FIGS. 1-3, the illustrated prior art stem collar 18 has a central bore to receive part of the bolt 16. The central bore has a central longitudinal axis defining an obtuse angle with at least one of the planes of the superior and inferior sides 33, 35 of the stem collar 18.

To ensure that the angle $\alpha$ remains in the illustrated orientation, the intercondylar box or boss 28 typically has a pair of anti-rotation tabs 46, 48 (see FIGS. 2 and 4) that mate with opposing flats 50, 52 on the femoral stem collars 18.

As commercially supplied, the stem members 14 and stem collars 18 are supplied as a unit, connected together prior to being supplied to the surgeon.

As shown in FIG. 1, on the tibial side, the tibial tray 13 of the modular tibial implant 11 comprises a tibial platform 53, with an integral stem 54 and integral keels 56 extending between the distal side of the tibial platform and the stem 54. The tibial platform 53 and stem 54 may have aligned bores to receive a distal extension of the tibial insert 15. In FIG. 1, the illustrated tibial platform and insert are configured for a fixed bearing, although it should be understood that these components could be configured so that the insert bearing 15 can rotate.

The distal end 58 of the tibial stem 54 has an interior surface with a threaded female opening (not shown). The threaded female opening mates with a plug (not shown) that can be used where a stem extension is not necessary, and can also be used with the illustrated tibial stem extension 17. The tibial stem extension 17 has a male threaded end 60 sized and shaped to mate with the threaded female opening at the distal end 58 of the stem 54.

For the tibial side, a typical existing implant kit for DePuy's P.F.C. SIGMA Knee System includes: four sizes of tibial stem extensions 17 for use in cemented applications, with diameters of 13 mm and 15 mm and lengths of 30 mm, 60 mm, 90 mm, 120 mm and 150 mm; twenty-four sizes of fluted tibial stem extensions 17 for non-cemented use, with diameters of 10 mm, 12 mm, 14, mm, 16 mm, 18 mm, 20 mm, 22 mm and 24 mm and lengths of 75 mm, 115 mm and 150 mm in each diameter. A variety of sizes of modular tibial trays 13 and inserts 15 are also included in the typical commercial kit. With this variety of modular components, the surgeon can customize the tibial side of the prosthesis to best fit the needs of the individual patient.

Variations on the knee implant system illustrated in FIGS. 1-4 have been disclosed. For example, posterior stabilized mobile bearing knees are disclosed in U.S. Pat. Nos. 6,727,723 B2 and 6,443,991. Adapters for such knee implant systems are disclosed in the following U.S. Pat. Nos. 6,171,342B1; 5,824,097; 5,782,921; and 5,182,921. U.S. Pat. Nos. 5,683,472 and 6,126,693 also disclose features related to knee implant systems. The disclosure of each of these patents is incorporated by reference herein in its entirety.

Although these prior knee implant systems have provided surgeons with great flexibility in meeting patient needs, and the modularity of these systems provides the opportunity to reduce the number of components needed in a surgical kit, these systems still require a substantial number of components.

SUMMARY OF THE INVENTION

The present invention addresses the need for a versatile modular knee implant system that offers surgeons many options to meet the needs of individual patients while reducing the number of components needed to provide these options.

In one aspect, the present invention provides a modular orthopaedic knee implant system. The system comprises a distal femoral component, a proximal tibial component, an adapter and a stem extension. The distal femoral component has a distal articulating surface and a proximal side. The proximal tibial component has a proximal surface and distal side. The adapter has a proximal end and a distal end; the distal end is sized and shaped to be capable of being connected to the proximal side of the distal femoral component. The stem extension has a connecting end, a body and an opposite end; the connecting end of the stem extension has external threads. The connecting end of the stem extension is sized and shaped to be capable of being selectively connected directly to the proximal tibial component and directly to the adapter.

In another aspect, the present invention addresses this need by providing an implantable orthopaedic adapter. The adapter comprises a first end, a second end, a first interior surface, a second interior surface and an outer surface. The first interior surface defines a first bore at the first end. The first bore has a central longitudinal axis. The second interior surface defines a second bore at the second end. The second bore also has a central longitudinal axis. The outer surface of the adapter tapers from one of the ends to the second end. At least one of the interior surfaces is threaded, and the central longitudinal axes of the first bore and second bore intersect at an acute angle.

In another aspect, the present invention addresses this need by providing a modular orthopaedic knee implant system comprising a distal femoral component, a proximal tibial component, a tibial bearing, a stem extension, a first femoral adapter, a second femoral adapter and a tapered metaphyseal sleeve. The distal femoral component has a distal articulating surface and a proximal side. The proximal tibial component has a proximal surface and a tibial side. The tibial bearing is carried by the proximal tibial component. The stem extension has a connecting end, a body and an opposite end. The first femoral adapter has a proximal end, a distal end, an interior surface defining a proximal bore and an interior surface defining a distal bore. The proximal bore and distal bore each have a central longitudinal axis. The central longitudinal axis of the distal bore defines an angle with the central longitudinal axis of the proximal bore when viewed in a plane extending in a medial-lateral direction. The second femoral adapter has a proximal end, a distal end, an interior, surface defining a proximal bore and an interior surface defining a distal bore. The proximal bore has a central longitudinal axis and the distal bore has a central longitudinal axis of the proximal bore. The central longitudinal axis of the distal bore defines an angle with the central longitudinal axis of the proximal bore when viewed in a plane extending in a medial-lateral direction; this angle of the second femoral adapter is different from the corresponding angle of the first femoral adapter. The tapered metaphyseal component has a proximal end and a distal end, an interior surface defining a distal bore at the distal end and an interior surface defining a proximal bore at the proximal end. The distal bore of the metaphyseal component is sized and shaped to be capable of selectively receiving at least a portion of each of the femoral adapters for selectively mounting the tapered metaphyseal component to the adapter. The connecting end of the stem extension is sized and shaped to be capable of being selectively connected directly to the proximal tibial component, to the proximal end of the first femoral adapter, to the proximal end of the second femoral adapter and to the proximal end of the tapered metaphyseal component.

BRIEF DESCRIPTION OF THE DRAWINGS

The features and advantages of the invention will be apparent from the following description and accompanying drawings, in which like reference numbers refer to the same parts throughout the different views.

FIG. 9 is a medial or lateral view of an example of an orthopaedic adapter incorporating the teachings of the present invention;

FIG. 10 is a distal end view of the orthopaedic adapter of FIGS. 9 and 11-12, taken along line 10-10 of FIG. 11;

FIG. 11 is an anterior or posterior view of the orthopaedic adapter of FIGS. 9-10 and 12;

FIG. 12 is a cross-section of the orthopaedic adapter of FIGS. 9-11, taken along line 12-12 of FIG. 9;

DETAILED DESCRIPTION

A modular orthopaedic knee implant system incorporating the principles of the present invention is illustrated in FIGS. 5-17 of the accompanying drawings. The illustrated modular orthopaedic knee implant system may include components of an existing knee implant system, along with new components that provide the orthopaedic surgeon with the flexibility to assemble a prosthetic knee implant that suits the needs of an individual patient, while reducing the overall inventory of components necessary to provide this flexibility.

Figure 1:
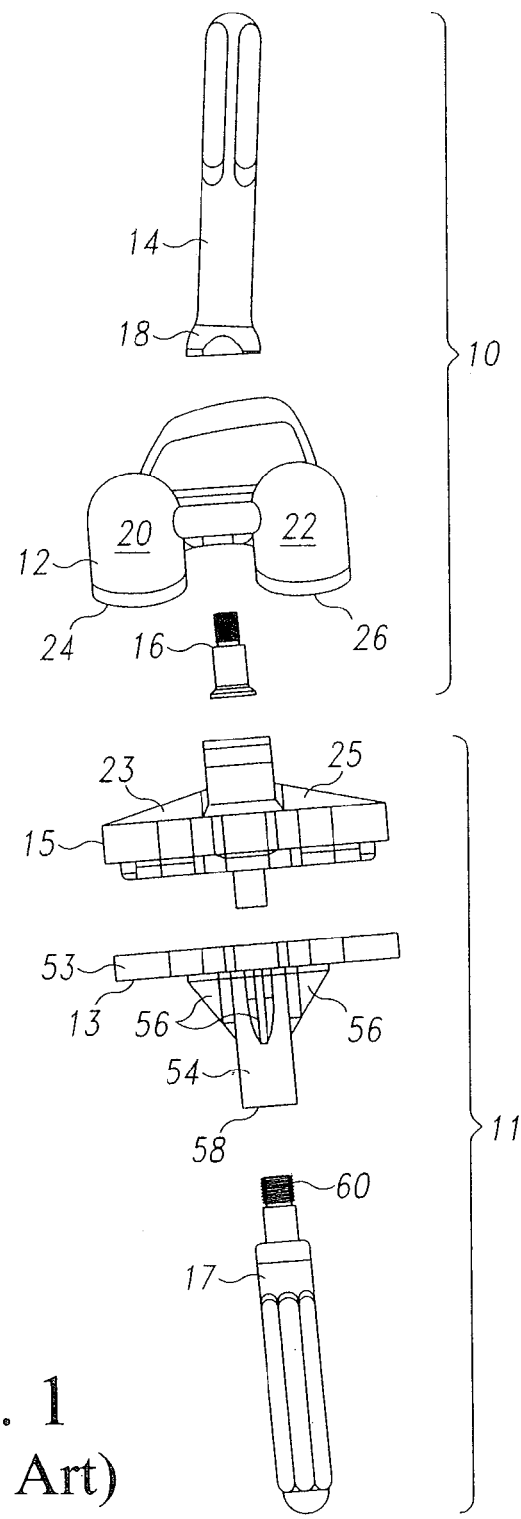
FIG. 1 is an exploded view of a prior art modular orthopaedic knee implant system.
Figure 2:
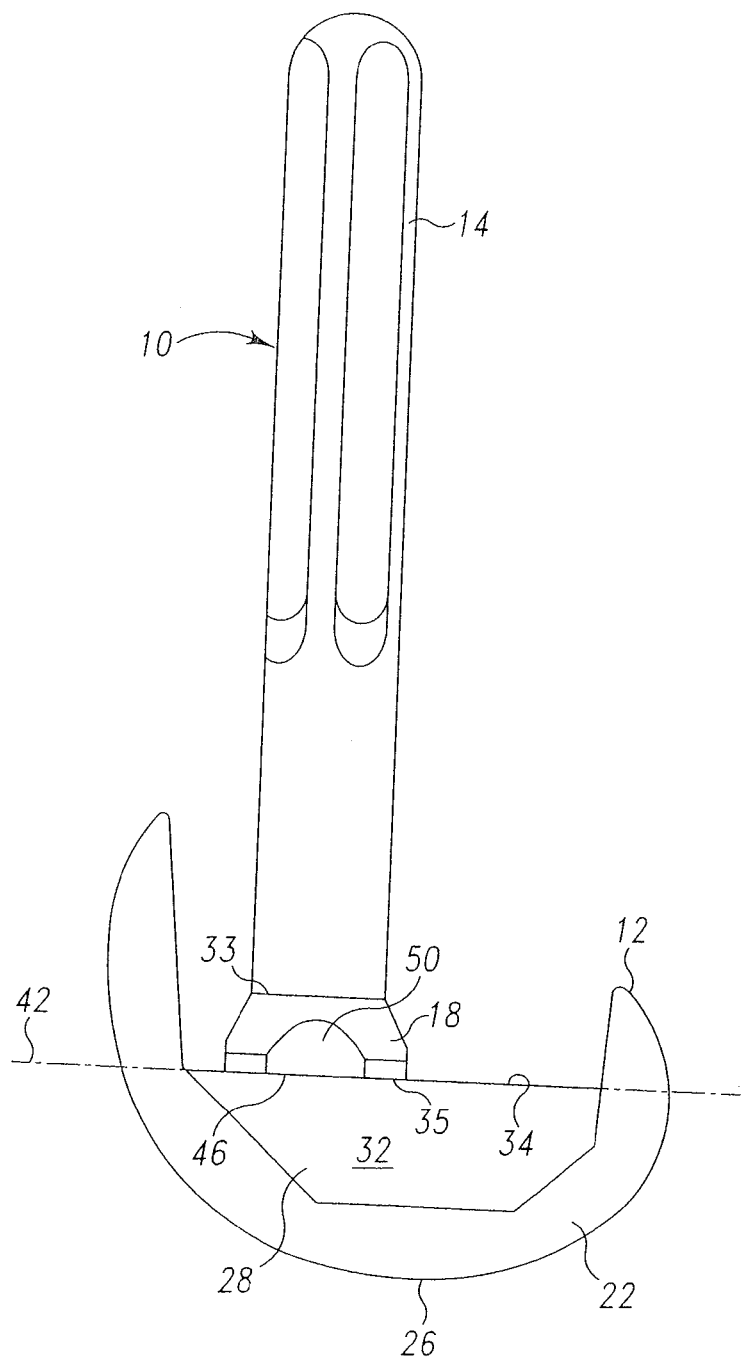
FIG. 2 is a lateral side view of the assembled femoral components of the modular orthopaedic knee implant system of FIG. 1.
Figure 3:
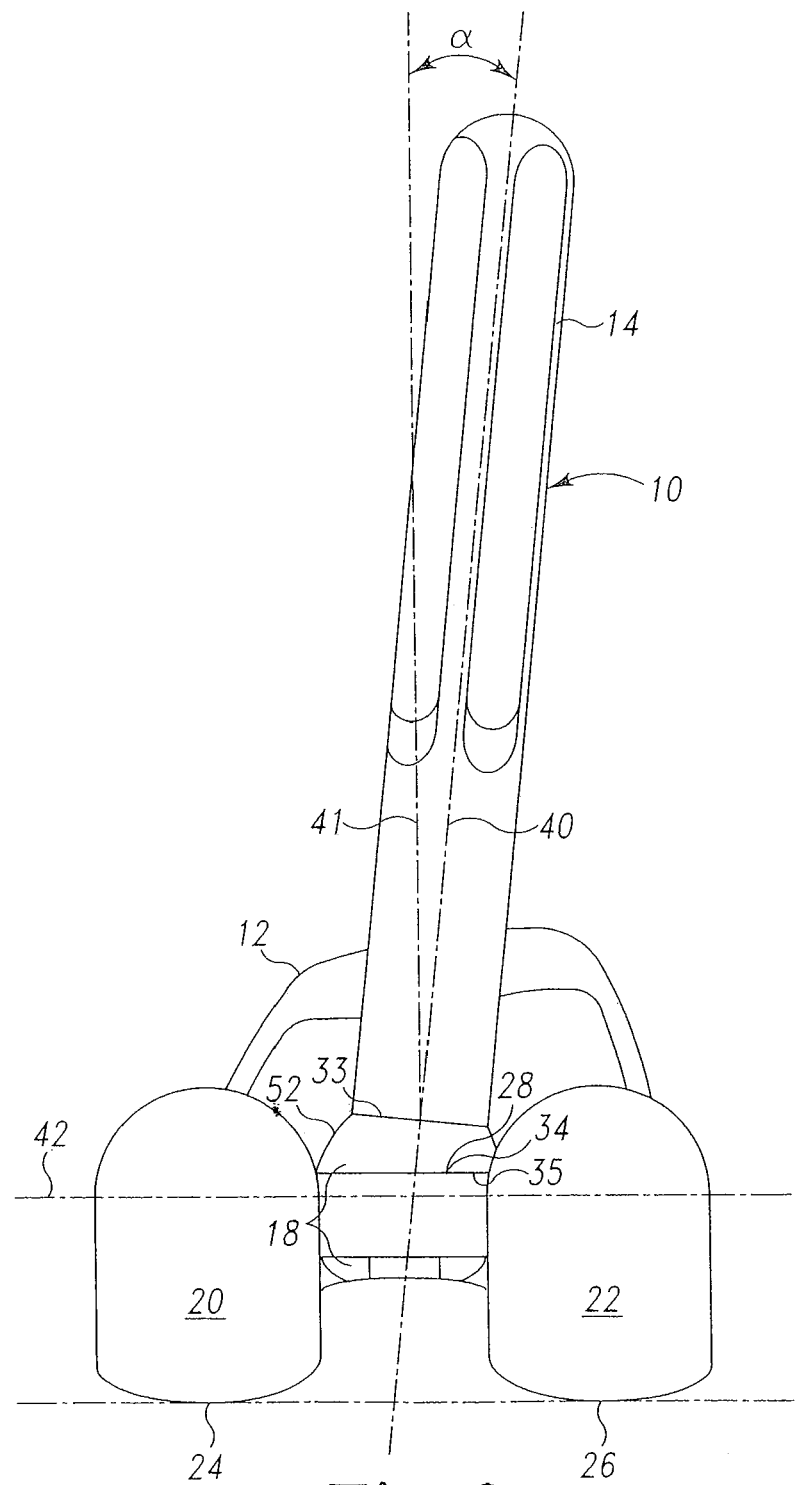
FIG. 3 is a posterior view of the assembled femoral components of the modular orthopaedic knee implant system of FIGS. 1-2.
Figure 4:
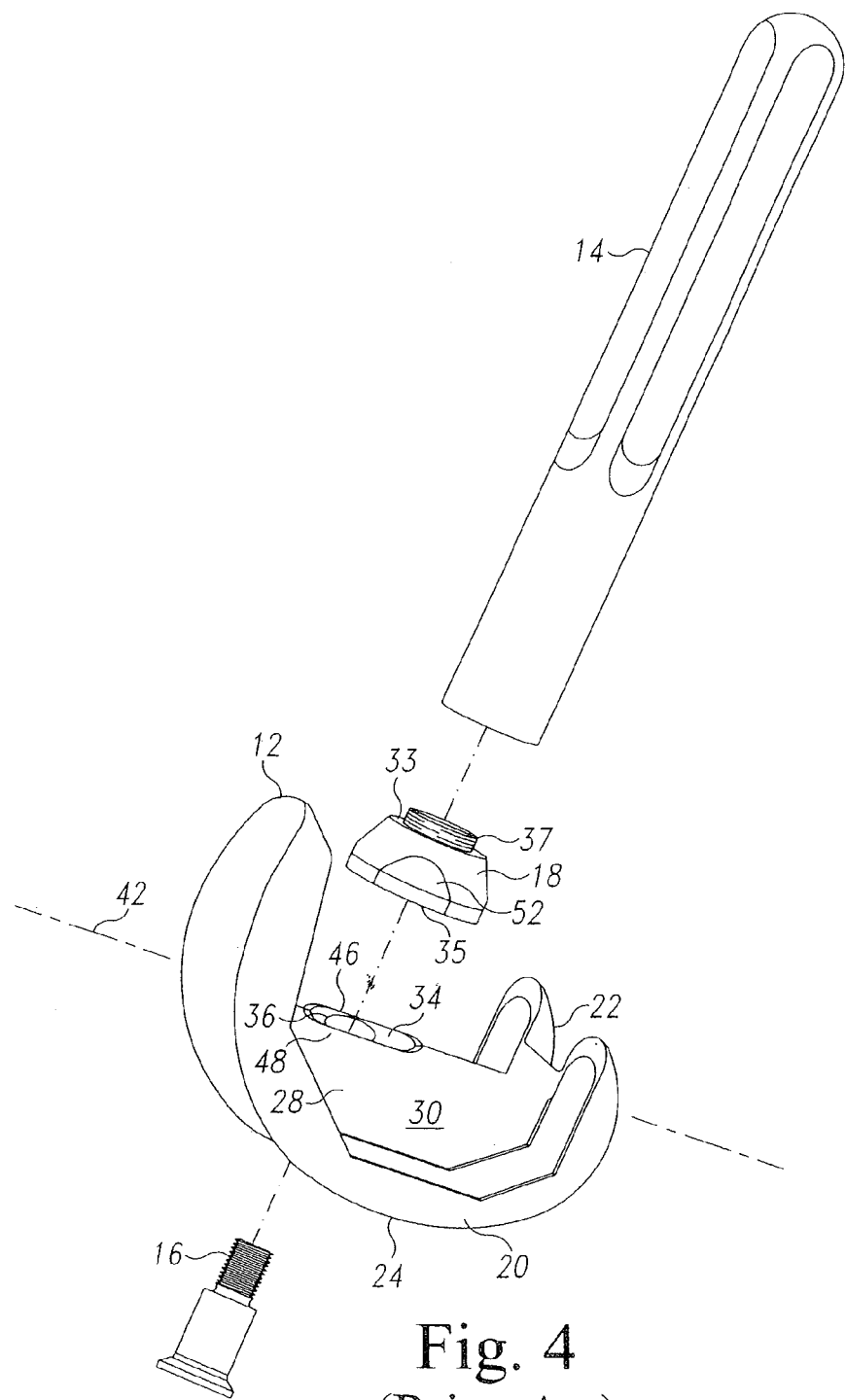
FIG. 4 is an exploded perspective view of the femoral components of the modular orthopaedic knee implant system of FIGS. 1-3.
Figure 5:
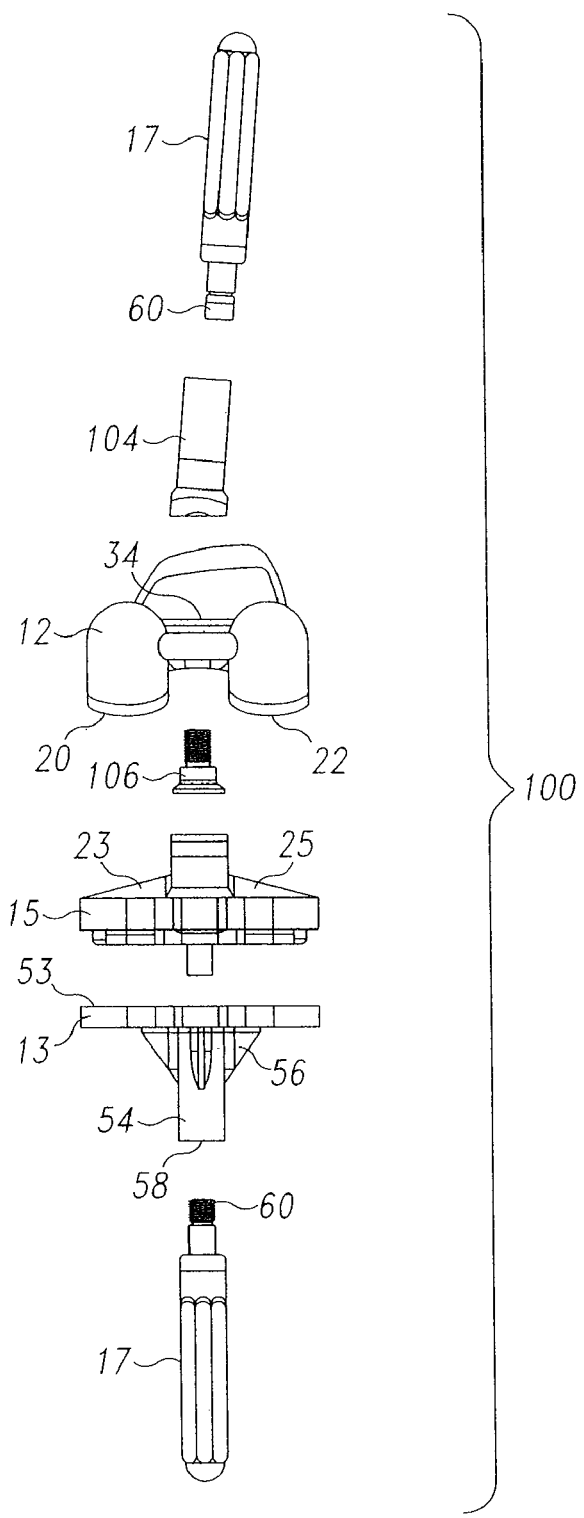
FIG. 5 is an exploded view of an example of a modular orthopaedic knee implant incorporating the teachings of the present invention.
Figure 6:
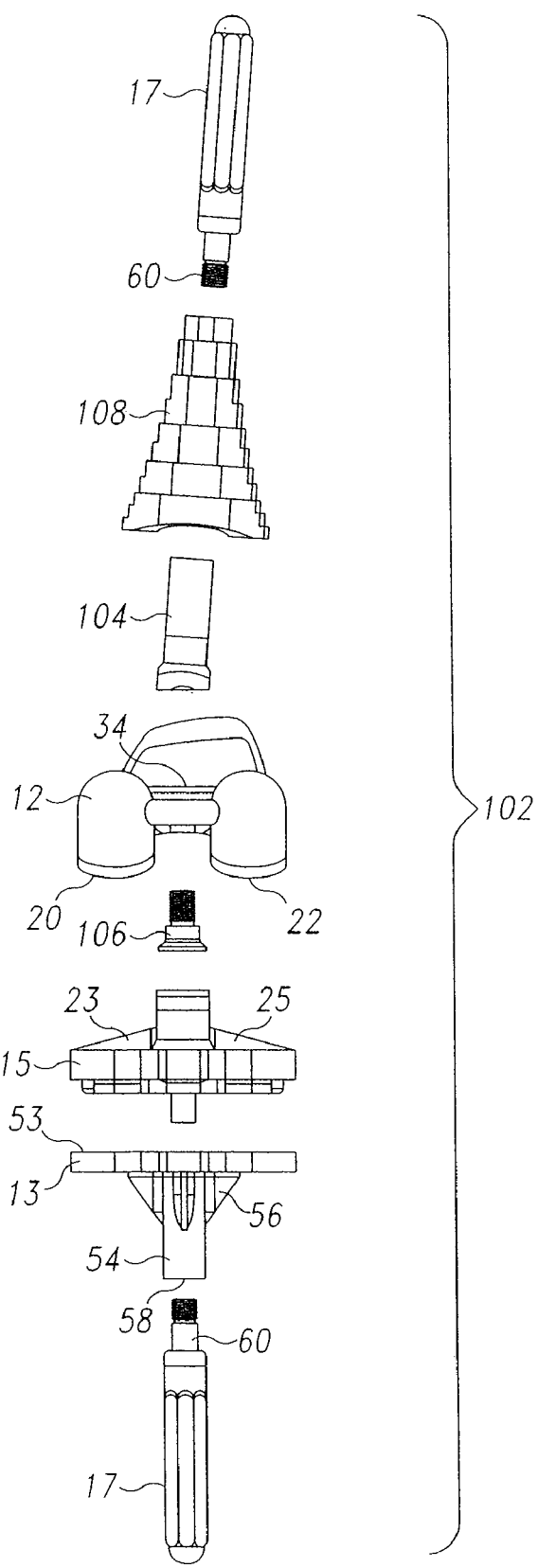
FIG. 6 is an exploded view of another example of a modular orthopaedic knee implant incorporating the teachings of the present invention.
Figure 7:
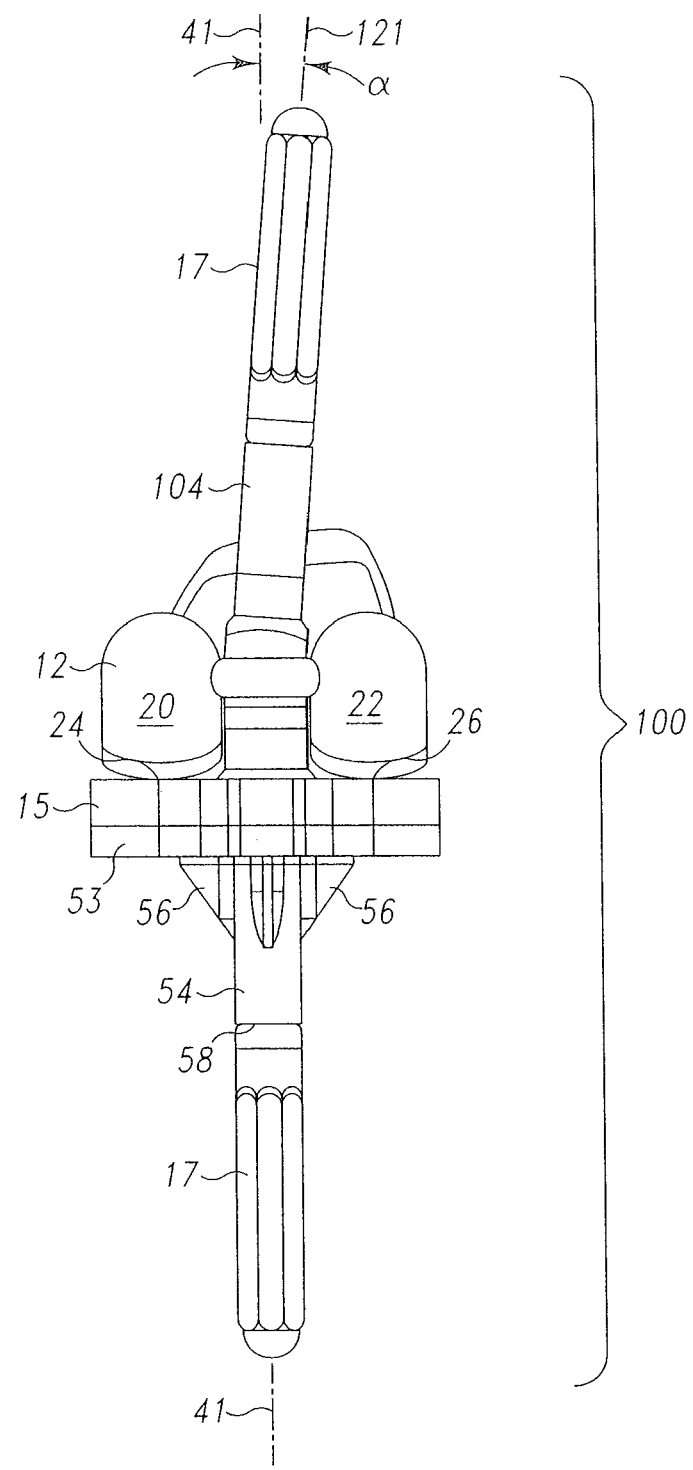
FIG. 7 is a posterior view of the assembled knee implant of FIG. 5.
Figure 8:
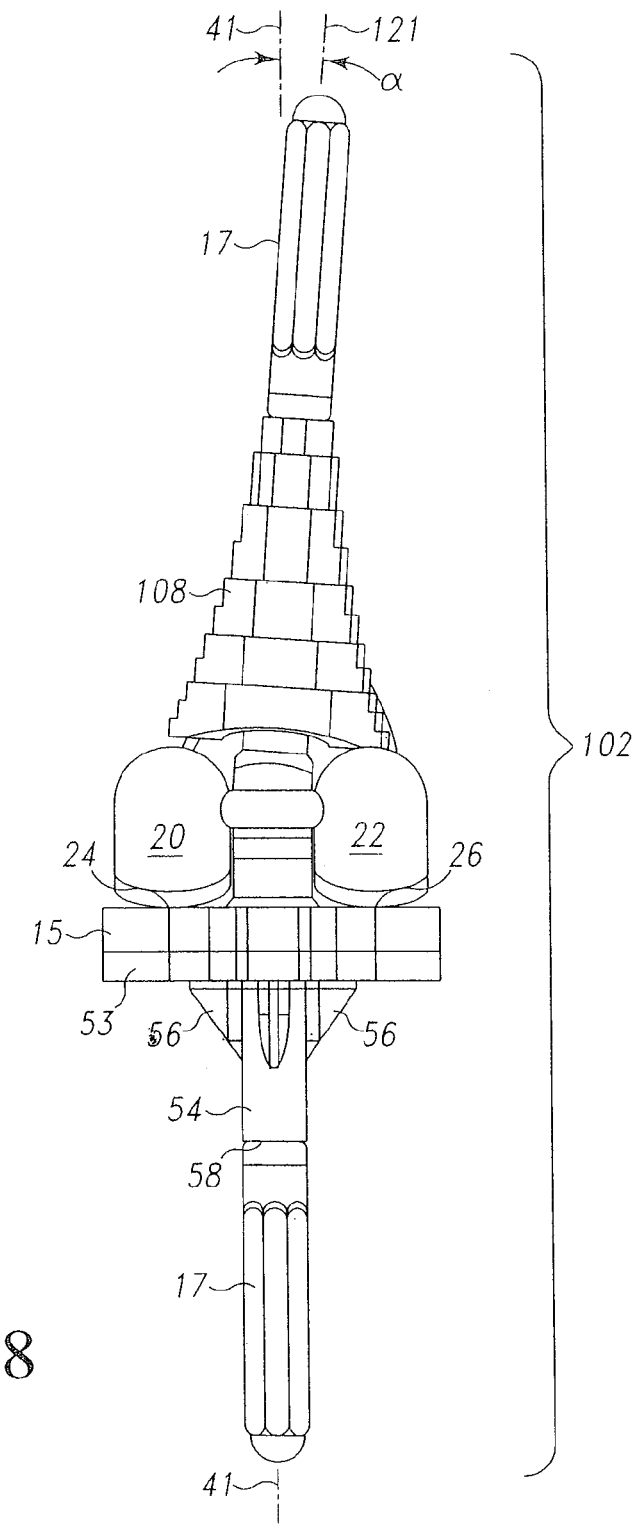
FIG. 8 is a posterior view of the assembled knee implant of FIG. 6.

FIGS. 5-6 illustrate, in exploded views, two exemplary orthopaedic knee implants 100, 102 that may be assembled by a surgeon using the knee implant system of the present invention. These knee implants 100, 102 are shown in FIGS. 7-8, respectively, in an assembled condition. It should be understood that FIGS. 5-8 illustrate implants for use in a patient's right leg; a mirror-image implant would also be used for the patient's left leg.

Each of the knee implants illustrated in FIGS. 5-8 includes: a femoral adapter 104; a distal femoral component 12; a femoral adapter bolt 106; a tibial insert 15; a tibial tray 13; and two stem extensions 17. As indicated by the use of the same reference numbers for the distal femoral component 12, tibial insert 15, tibial tray 13, and two stem extensions 17, these components of the implants may have the same features as the prior art system illustrated in FIGS. 1-4 and sold by DePuy Orthopaedics, Inc. of Warsaw, Ind. as part of the P.F.C. SIGMA® Knee Implant System. It should be understood that this system is identified as an example only; the present invention is not limited to any particular brand or type of knee implant system unless expressly called for in the claims.

However, unlike the prior art knee implant system illustrated in FIGS. 1-4, the knee implants 100, 102 and implant kit of the present invention do not require the use of a separate set of stem extensions for the femoral portion of the implant. With the present invention, the stem extensions 17 previously used only for the tibial portion of the implant can also be used for the femoral side, substantially reducing the number of components needed.

The knee implant 102 illustrated in FIGS. 6 and 8 includes an additional component, a metaphyseal sleeve 108. The metaphyseal sleeve 108 may have features such as those disclosed in U.S. Provisional Patent Application Ser. No. 60/523,170 filed on Nov. 18, 2003 and entitled Modular Implant System with Fully Porous Coated Sleeve, the disclosure of which is incorporated by reference herein in its entirety. Alternatively, the metaphyseal sleeve 108 may have features of commercially available sleeves sold by DePuy Orthopaedics, Inc. as part of its LCS® Total Knee Implant System. However, it should be understood that the present invention is not limited to any particular metaphyseal sleeve unless expressly called for in the claims.

Figure 13:
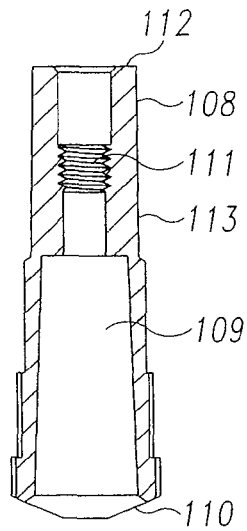
FIG. 13 is a cross-section of an exemplary metaphyseal sleeve that may be used with the implant and system of the present invention.

As illustrated in FIG. 13, the metaphyseal sleeve 108 may include a Morse taper bore 109 at its distal end 110 and a threaded female bore 111 at or near its proximal end 112. The outer surface 113 of the illustrated sleeve 108 has a stepped configuration, tapering from the distal end 110 toward the proximal end 112. The outer surface 113 of the sleeve may be partially porous, or may be fully porous as disclosed in U.S. Provisional Patent Application Ser. No. 60/523,170.

The metaphyseal sleeve 108 is selectively mountable on the femoral adapter 104. As shown in FIGS. 9 and 11-12, the outer surface of the femoral adapter 104 includes a tapered portion 114 at its proximal end. The tapered portion 114 of the outer surface is sized and shaped to frictionally lock with the Morse taper female bore 109 of the metaphyseal sleeve 108.

Typically, the tapered portion 114 of the outer surface would taper at an angle of 5-8° to define a Morse taper post to be received within and lock with the Morse taper bore 109 of the metaphyseal sleeve 108.

As shown in FIG. 12, at its proximal end 116, the femoral adapter 104 has a proximal female bore 115 with interior walls defining a lead-in chamfer 117, a cylindrical portion 119 and a threaded female portion 118. The threaded female portion 118 is sized and shaped to receive and engage the threaded male end 60 of the stem extension 17. The threads may be formed so as to lock together on engagement, such as through use of a SPIRALOCK® threaded engagement. The proximal female bore 115 has a central longitudinal axis 121.

As shown in FIG. 12, at or near its distal end 122, the femoral adapter 104 has a distal female bore 123 with interior walls defining a chamfer portion 127, a cylindrical portion 129 and a threaded female portion 124. The threaded female portion 124 is sized and shaped to receive and engage the threaded male end 126 of the femoral bolt 106, shown in FIGS. 14-15. These threads may also be formed so as to lock together on engagement, such as through use of a SPIRALOCK® threaded engagement. The distal female bore 123 has a central longitudinal axis 125 that intersects the central longitudinal axis 121 of the proximal female bore 115 at an angle β.

The femoral adapter 104 has an annular boss-engaging surface 128 at its distal end 122. This boss-engaging surface 128 may be generally perpendicular to the axis 125 of the distal female bore 123. In the illustrated embodiment, the boss-engaging surface 128 is canted at an angle δ to a transverse plane 130. The transverse plane 130 is perpendicular to the axis 121 of the proximal female bore 115. In the illustrated embodiment, the angles β and δ are equal to each other, and are about 5°. Alternatively, the angles β and δ could be about 3° or 7°. In the embodiment where δ is 7°, the axis 125 of the distal female bore 123 may be tilted at an angle of 2° relative to the boss-engaging surface 128. It should be understood that these angles are provided as examples only; the invention is not limited to any particular angle unless expressly set forth in the claims.

When assembled, the boss-engaging surface 128 of the femoral adapter 104 engages the mounting platform 34 of the intercondylar boss or box 28 of the femoral component 12. Thus, the angles β and δ set the valgus angle of the femoral adapter 104, and thereby set the valgus angle of the femoral stem extension, as discussed in more detail below. The distal end of the femoral adaptor 104 may have features of the femoral stem collar 18 of the existing P.F.C. SIGMA knee implant system.

Figure 14:
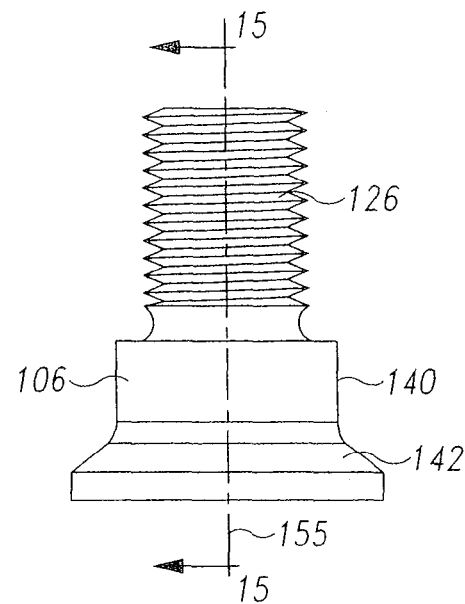
FIG. 14 is a side view of an example of a bolt that may be used with the orthopaedic adapter of FIGS. 9-12.
Figure 15:
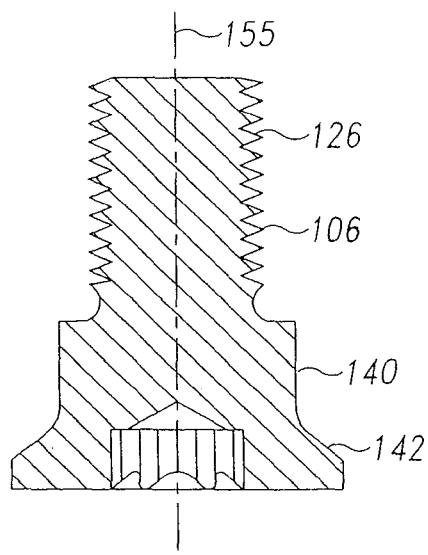
FIG. 15 is a cross-section of the bolt of FIG. 14, taken along line 15-15 of FIG. 14.
Figure 16:
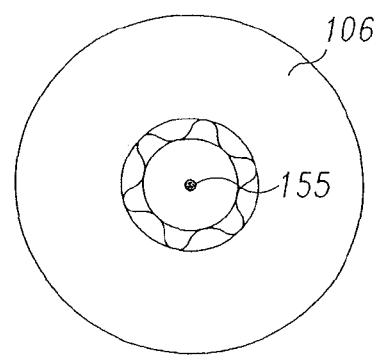
FIG. 16 is an end view of the bolt of FIGS. 14-15.

To lock the femoral adapter 104 to the distal femoral component 12, the bolt 106 of FIGS. 14-15 is used in the illustrated embodiments. In addition to the threaded male end 126, the bolt 106 includes a head with a cylindrical portion 140 and a tapered portion 142. The cylindrical portion 140 and tapered portion 142 of the bolt head are sized and shaped to be received within the cylindrical portion 129 and chamfer portion 127 of the distal female bore 123 of the femoral adapter 104 and the opening 36 of the mounting platform 34 of the femoral component 12. The tapered portion 142 of the bolt may be frustoconical or could be spherically shaped as disclosed in U.S. Pat. No. 5,556,433, for example, which is incorporated by reference herein in its entirety.

Figure 17:
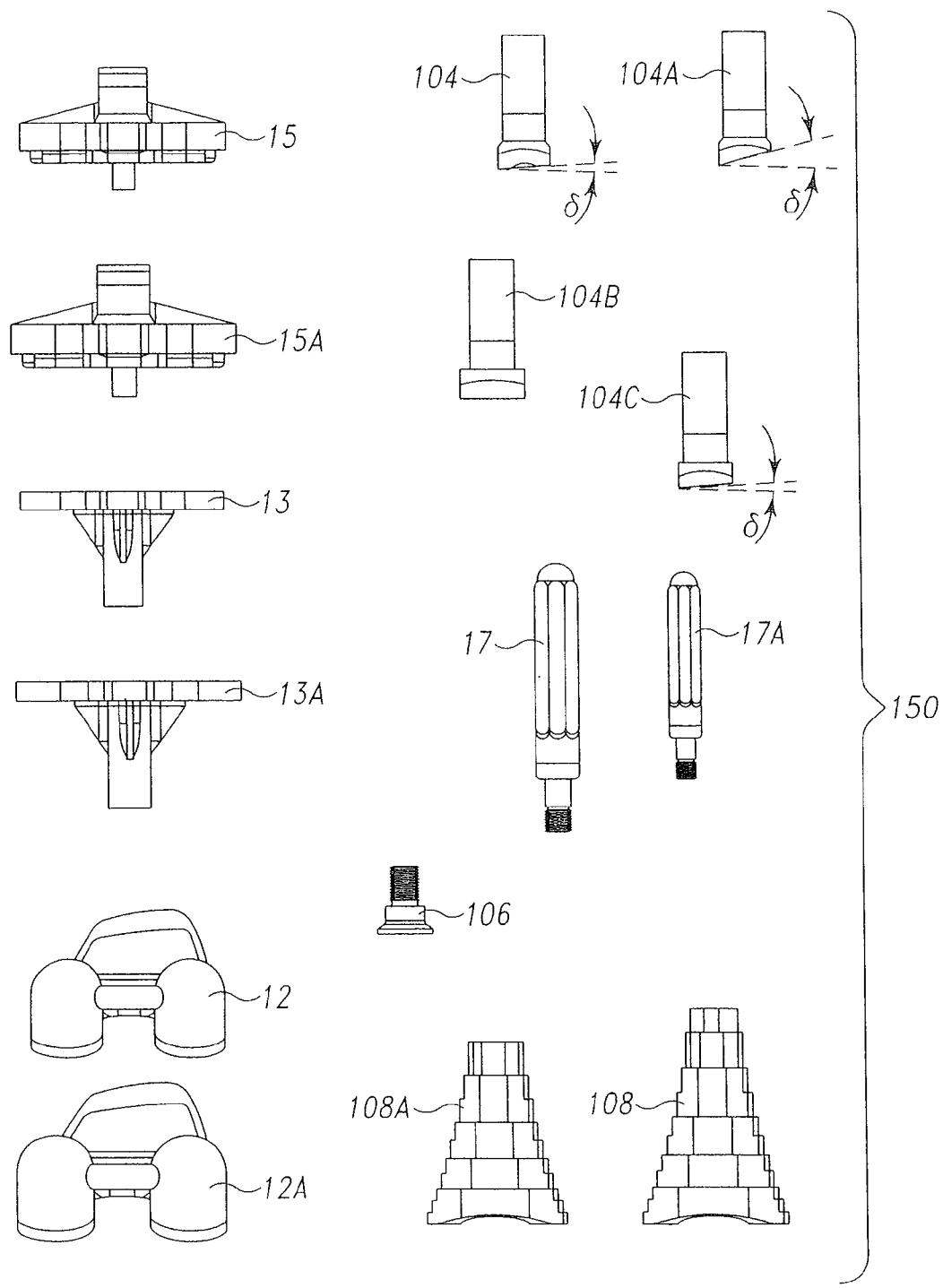
FIG. 17 is a view of an example of modular orthopaedic knee implant system or kit incorporating the teachings of the present invention.
Figure 18:
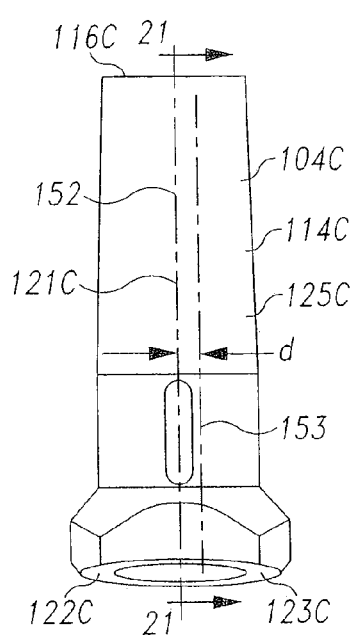
FIG. 18 is a medial or lateral view of another example of an orthopaedic adapter that can be included in the modular orthopaedic knee implant system or kit of the present invention to allow for anterior and posterior offset of the femoral stem.

An example of a knee implant system 150 incorporating the above-described components is illustrated in FIG. 17. The illustrated knee implant system 150 includes a plurality of distal femoral components 12, 12A of different sizes; a plurality of tibial trays 13, 13A of different sizes; a plurality of tibial insert bearings 15, 15A of different sizes; a plurality of metaphyseal sleeves 108, 108A of different sizes; a bolt 106 (additional bolts such as offset bolts could also be included); a plurality of stem extensions 17, 17A of different characteristics (such as different lengths, different diameters, or different shapes adapted to cemented and non-cemented use); and a plurality of femoral adapters 104, 104A, 104B, 104C. It should be understood that a typical knee implant system 150 would also include additional femoral and tibial components 12, 13, 15 of different sizes for use on the knee of the other leg of the patient. In the illustrated system 150, three femoral adapters 104, 104A, 104B are provided to give the surgeon the option of selecting an angle δ of 5°, 7° or 0°, for example. As described below, one or more additional femoral adapters 104C may also be included to give the surgeon the option of selecting an anterior or posterior offset. One advantage of the illustrated system 150 is that one set of stem extensions can be used on both the tibial and femoral sides. Accordingly, the number of stem extensions provided in the kit or system can be reduced without reducing the options available to the surgeon. With the inclusion of metaphyseal sleeves 108, 108A in the system, even greater options are available to the surgeon, while the number of stem extensions need not be increased.

To provide further options to suit individual patient needs, the knee implant system or kit 150 could include an anterior-posterior offset femoral adapter 104C illustrated in FIGS. 18-21 and 23. Like the femoral adapter 104 described above with reference to FIGS. 9-12, the outer surface of the anterior-posterior offset femoral adapter 104C has a tapered portion 114C at its proximal end, sized and shaped to frictionally lock with a Morse taper female bore 109 of a metaphyseal sleeve 108 (see FIG. 13). And like the embodiment of FIGS. 9-12, the anterior-posterior offset femoral adapter 104C has a proximal female bore 115C (see FIGS. 21 and 23) at or near its proximal end 116C with interior walls defining a lead in chamfer 117C, a cylindrical portion 119C and a threaded female portion 118C. The threaded female portion 118C is sized and shaped to receive and engage the threaded male end 60 of the stem extension 17.

At or near its distal end 122C, the anterior-posterior offset femoral adapter 104C has a distal female bore 123C (see FIGS. 21 and 23) with interior walls defining a lead-in chamfer portion 127C, a cylindrical portion 129C and a threaded female portion 124C. The threaded female portion 124C is sized and shaped to receive the threaded male end 126 of the femoral bolt 106.

The distal female bore 123C of the anterior-posterior offset femoral adapter has a central longitudinal axis 125C. As in the embodiment of FIGS. 9-12, this axis 125C of the distal female bore 123C defines an angle β with the central longitudinal axis 121C of the proximal female bore 115C (see FIG. 21) when viewed in a central medial-lateral or coronal plane (labeled 152 in FIGS. 10 and 19). Like the embodiment of FIGS. 9-12, the boss-engaging surface 128C is canted at an angle δ to a transverse plane 130C when viewed in a medial-lateral or coronal plane (labeled 152 in FIGS. 10 and 19). As in the embodiment of FIGS. 9-12, the angles β and δ could be, for example, 0°, 3°, 5° or a kit could include anterior-posterior offset femoral adapters with all of these angles. It should be understood that the angles β and δ also correspond with the valgus angle, shown as angle α in FIGS. 3 and 7-8. It should also be understood that these angles are provided as examples only; the present invention is not limited to any particular angle unless expressly set forth in the claims.

Figure 22:
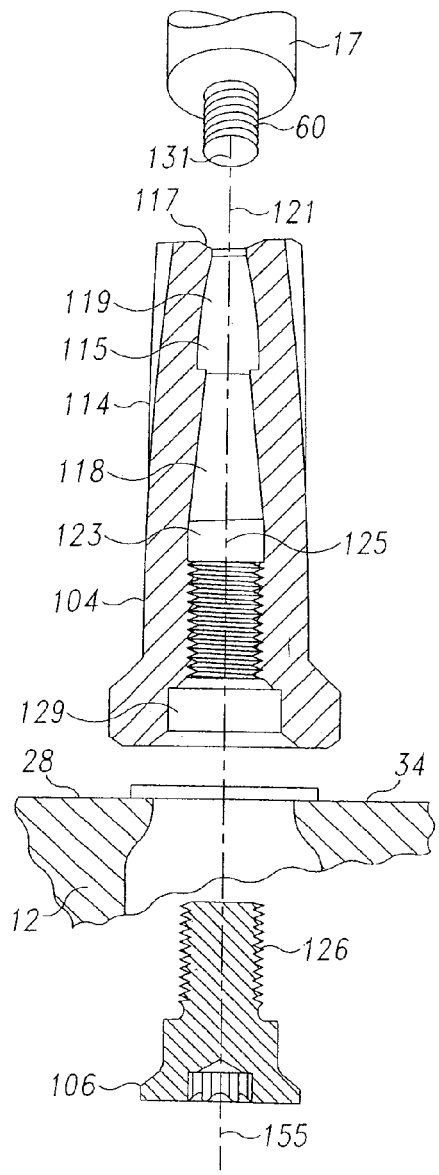
FIG. 22 is an exploded view of the orthopaedic adapter of FIGS. 9-12 in combination with a stem extension, femoral implant component and bolt, with parts shown in cross-section through an anterior-posterior or sagittal plane.
Figure 23:
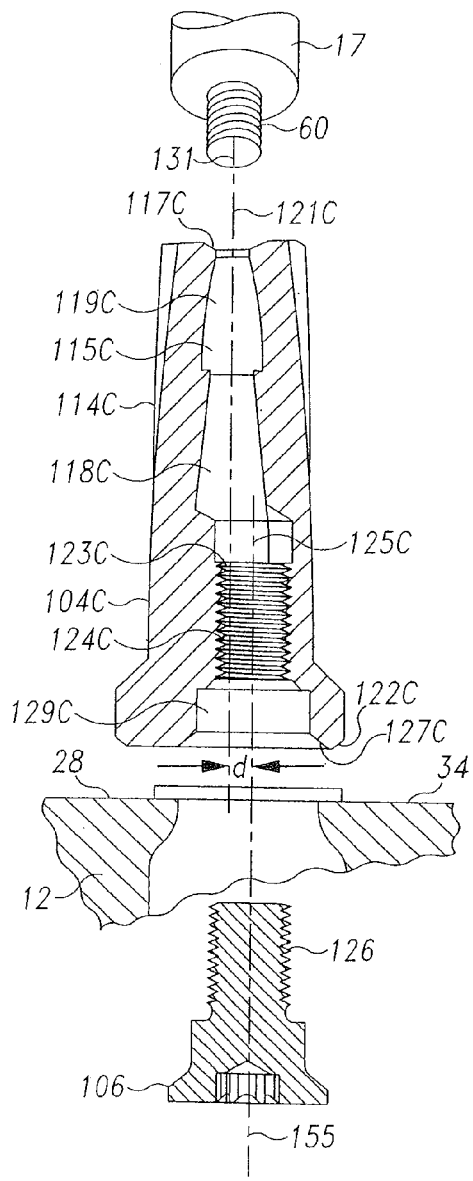
FIG. 23 is an exploded view of the orthopaedic adapter of FIGS. 18-21 in combination with a stem extension, femoral implant component and bolt, with parts shown in cross-section through an anterior-posterior or sagittal plane.

However, the embodiments of FIGS. 9-12 and FIGS. 18-21 differ when viewed in an anterior-posterior or sagittal plane (labeled 154 and 154C in FIGS. 10 and 19), as can be seen from a comparison of FIGS. 22 and 23. The femoral adapters 104 and 104C are shown in FIGS. 22 and 23 in exploded views in combination with a stem extension 17, femoral implant component 12 and bolt 106. FIG. 22 illustrates the femoral adapter 104 of FIGS. 9-12 and FIG. 23 illustrates the femoral adapter 104C of FIGS. 18-21.

As can be seen in FIG. 22, in the case of the femoral adapter 104 of FIGS. 9-12, the central longitudinal axis 131 of the threaded end 60 of the stem extension 17 is aligned co-linearly with the central longitudinal axis 121 of the proximal female threaded bore 115, the central longitudinal axis 125 of the distal threaded female bore 123 and the central longitudinal axis 155 of the bolt 106 when viewed in an anterior-posterior or sagittal plane. Thus, as shown in FIG. 10 for the femoral adapter of FIGS. 9-12, the central longitudinal axes 121, 125 of both the proximal female threaded bore 115 and the distal female threaded bore 123 lie in the same central medial-lateral or coronal plane 152.

Figure 19:
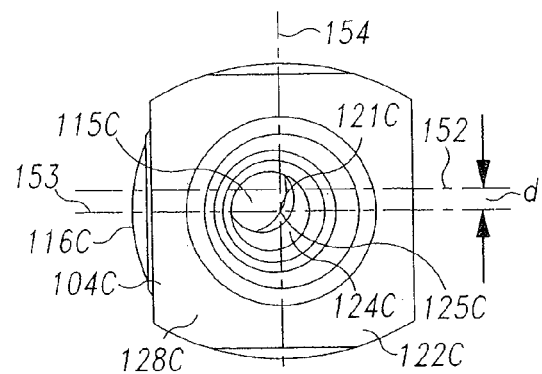
FIG. 19 is a distal end view of the orthopaedic adapter of FIGS. 18, 20-21 and 23, taken along line 19-19 of FIG. 20.
Figure 20:
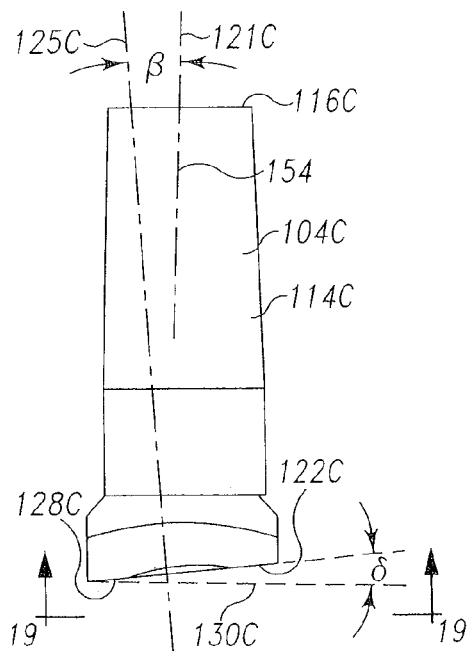
FIG. 20 is an anterior or posterior view of the orthopaedic adapter of FIGS. 18-19, 21 and 23.
Figure 21:
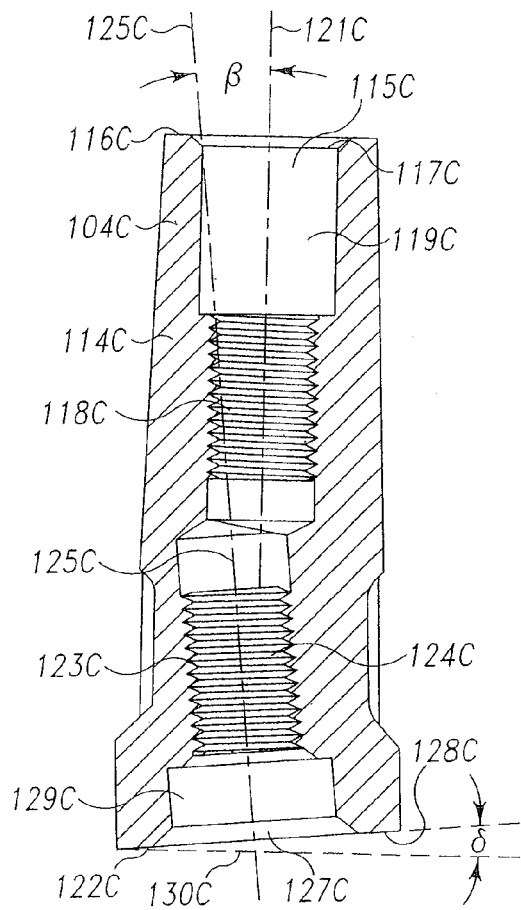
FIG. 21 is a cross-section of the orthopaedic adapter of FIGS. 18-20 and 23, taken along line 21-21 of FIG. 18.

But as can be seen in FIG. 23, in the case of the anterior-posterior offset femoral adapter 104C of FIGS. 18-21, the central longitudinal axis 131 of the threaded end 60 of the stem extension 17 is aligned co-linearly only with the central longitudinal axis 121C of the proximal female threaded bore 115C. The central longitudinal axis 125C of the distal female bore 123C and the central longitudinal axis 155 of the bolt 106 are co-linearly aligned, but are offset by a distance "d" (see FIGS. 18-19 and 23) from the central longitudinal axes 131, 121C of the end 60 of the extension 17 and the proximal female bore 115C. This distance "d" equates with an offset in the anterior-posterior direction. FIG. 19 illustrates this distance "d" as the distance between the central medial-lateral or coronal plane 152 of the central longitudinal axis 121C of the proximal female bore 115C and the parallel coronal plane 153 of the central longitudinal axis 125C of the distal female bore 123C. Thus, using the anterior-posterior offset femoral adapter of the embodiment of FIGS. 18-21 and 23, the position of the stem extension 17 can be offset in either the anterior or posterior direction. A typical example of a dimension for distance "d" is on the order of 2 mm, but it should be understood that this distance is provided as an example only; the invention is not limited to a particular dimension for the distance "d" unless expressly set forth in the claims.

To provide an offset in the anterior direction, the anterior-posterior offset femoral adapter 104C would be used on the left knee. To provide an offset in the posterior direction, the anterior-posterior femoral adapter 104C would be used on the right knee. To allow for such offsets in both the anterior and posterior directions for both knees, a typical surgical kit would include an anterior-posterior femoral adapter 104C as illustrated in FIGS. 18-21 and 23 and would also include an anterior-posterior femoral adapter similar to that illustrated in FIGS. 18-21 and 23 but with the position of the central longitudinal axis of the distal female bore offset to the left of the central axis of the proximal female bore, instead of to the right as shown in FIG. 23.

Figure 24:
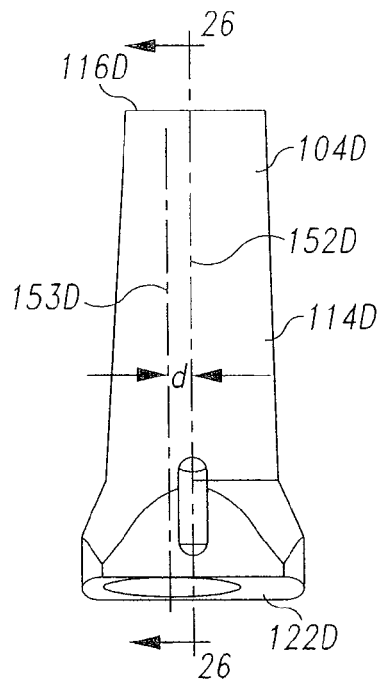
FIG. 24 is a medial or lateral view of another example of an orthopaedic adapter that can be included in the modular orthopaedic knee implant system or kit of the present invention to allow for anterior and posterior offset of the femoral stem.
Figure 25:
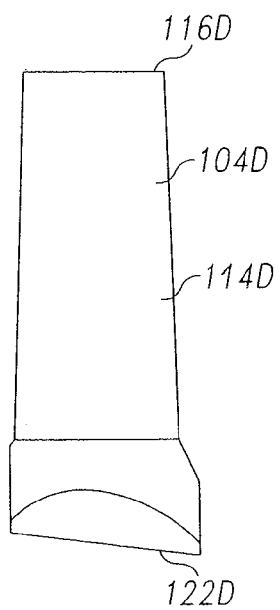
FIG. 25 is an anterior or posterior view of the orthopaedic adapter of FIG. 24.
Figure 26:
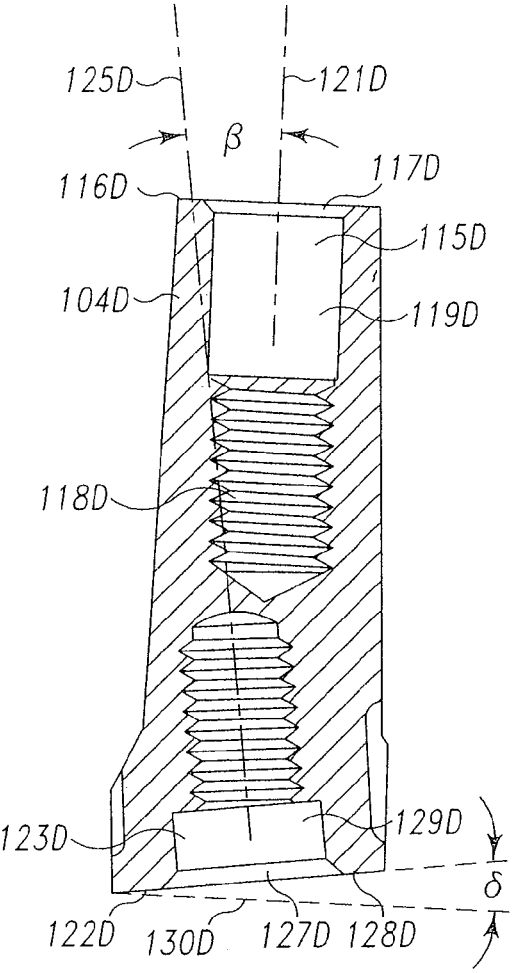
FIG. 26 is a cross-section of the orthopaedic adapter of FIGS. 24-25, taken along line 26-26 of FIG. 24.

Another embodiment of a femoral adapter is illustrated in FIGS. 24-26 at 104D. The femoral adapter 104D of this embodiment is similar to the femoral adapter 104C of FIGS. 18-21, except that the exterior surfaces of the adapters 104, 104C, 104D are shaped slightly differently. In FIGS. 24-26, the reference numbers used for the embodiments of FIGS. 9-12 and 18-21 have also been used, followed by the letter "D", to indicate similar features or portions of the adapters.

In the embodiments of FIGS. 9-12 and 18-21, the femoral adapters 104, 104C include a cylindrical outer surface 160, 160C between the tapered outer surface 114, 114C of the proximal end portion 116, 116C and the distal end 122, 122C.

In the embodiment of FIGS. 24-26, the outer surface is tapered from the proximal end 116D to the mounting portion at the distal end 122D; there is no intermediate cylindrically shaped portion. The angle of the tapered outer surface 114D in the embodiment of FIGS. 24-26 may be sized and shaped to frictionally lock with the Morse taper female bore 109 of the metaphyseal sleeve 108.

Although the embodiment of FIGS. 24-26 is illustrated with an anterior-posterior offset similar to the adapter 104C of FIGS. 18-21, it should be understood that an adapter with the extended tapered exterior surface of FIGS. 24-26 could have the features of the adapter 104 of FIGS. 8-12 so that no anterior-posterior offset is provided. It should also be understood that a surgical kit or knee implant system could include several adapters having the exterior surface shape shown in FIGS. 24-26.

All of the components of the illustrated knee implant system 150 can be made of standard materials, such as titanium or a cobalt-chrome alloy. The components can be made and finished in standard ways, and may include porous coatings where desired.

As is typical in known orthopaedic implant systems, a number of trials would also be included in the kit to give the surgeon the opportunity to evaluate the implants selected before permanently implanting the implant components.

In use, the surgeon will prepare the patient's femur and tibia in a standard manner. If the surgeon determines that it is desirable to include a stem extension 17 on either the tibial side or femoral side, an appropriately sized and finished stem extension 17 can be selected from the kit or system. For the tibial side, the surgeon can simply thread the stem extension onto the distal end of the tibial tray 13. For the femoral side, if a stem extension is desired the surgeon would select the appropriate femoral adapter 104, 104C or 104D and affix the selected adapter to the mounting surface 34 of the intercondylar box or boss 28 with the bolt 106. If the patient's condition does not warrant use of a metaphyseal sleeve 108, the surgeon can thread an appropriately sized and finished stem extension 17 onto the proximal end of the femoral adapter 104, 104C, 104D. If the patient's condition warrants use of a metaphyseal sleeve 108, the surgeon can fix an appropriately sized and finished sleeve 108 onto the femoral adapter 104, 104C, 104D through the Morse taper connection and then can thread an appropriately sized and finished stem extension 17 onto the proximal end of the metaphyseal sleeve 108.

Various modifications and additions can be made to the above-described embodiments of the invention without departing from the spirit of the invention. All such modifications and additions are intended to fall within the scope of the claims unless the claims expressly call for a specific feature or construction.

I claim:

1. A modular orthopaedic knee implant system comprising:
   a distal femoral component having a distal articulating surface and a proximal side;
   a proximal tibial component having a proximal surface and distal side;
   an adapter having a proximal end and a distal end, wherein the distal end is sized and shaped to be capable of being connected to the proximal side of the distal femoral component; and
   a stem extension having a connecting end, a body and an opposite end, the connecting end having external threads;

wherein the connecting end of the stem extension is sized and shaped to be capable of being selectively connected directly to the proximal tibial component and directly to the adapter; and wherein the adapter includes: a distal interior surface defining a distal bore at the distal end of the adapter, the distal bore having a central longitudinal axis; and a proximal interior surface defining a proximal bore at the proximal end of the adapter, the proximal bore having a central longitudinal axis defining an acute angle with the central longitudinal axis of the distal bore when viewed in a plane extending in a medial-lateral direction; wherein the proximal interior surface of the proximal bore is threaded.

2. The modular orthopaedic knee implant system of claim 1 further comprising a tapered metaphyseal component having a proximal end and a distal end, an interior surface defining a distal bore at the distal end, an interior surface defining a proximal bore at the proximal end, wherein the distal bore is sized and shaped to be capable of receiving at least a portion of the adapter for mounting the tapered metaphyseal component to the adapter, and the proximal bore is sized and shaped to be capable being connected to the connecting end of the stem extension.

3. The modular orthopaedic knee implant system of claim 2 wherein the adapter has an outer surface and wherein the outer surface of the adapter and the distal bore of the tapered metaphyseal component are sized and shaped to frictionally lock together when assembled.

4. The modular orthopaedic knee implant system of claim 1 wherein the body of the stem extension is sized and shaped so as to be capable of being received within the intramedullary canal of the femur and within the intramedullary canal of the tibia.

5. The modular orthopaedic knee implant system of claim 1 wherein the connecting end of the stem extension has exterior threads.

6. The modular orthopaedic knee implant system of claim 5 wherein the proximal end of the adapter has an interior surface defining a proximal bore at its proximal end, wherein the interior surface defining the proximal bore is threaded.

7. The modular orthopaedic knee implant system of claim 1 wherein the central longitudinal axis of the distal bore and the central longitudinal axis of the proximal bore are co-linear when viewed in a plane extending in an anterior-posterior direction.

8. The modular orthopaedic knee implant system of claim 1 wherein the central longitudinal axis of the distal bore is offset from and parallel to the central longitudinal axis of the proximal bore when viewed in a plane extending in an anterior-posterior direction.

9. The modular orthopaedic knee implant system of claim 1 wherein the adapter includes a proximal end surface lying in one plane and a distal end surface lying in a non-parallel plane.

10. The modular orthopaedic knee implant system of claim 1 further comprising a second adapter having a proximal end and a distal end, wherein the distal end is sized and shaped to be capable of being connected to the proximal side of the distal femoral component, wherein each adapter has a proximal end surface lying in one plane and a distal end surface lying in a non-parallel plane, and wherein the planes of the distal end surfaces of the two adapters define different angles with the planes of the proximal end surfaces.

11. The modular orthopaedic knee implant system of claim 1 further comprising a plurality of stem extensions.

12. A modular orthopaedic knee implant system comprising:
a distal femoral component having a distal articulating surface and a proximal side;
a proximal tibial component having a proximal surface and a tibial side;
a tibial bearing to be carried by the proximal tibial component;
a stem extension having a connecting end, a body and an opposite end;
a femoral adapter having a proximal end, a distal end, an interior surface defining a proximal bore and an interior surface defining a distal bore, wherein the proximal bore and distal bore of the adapter each has a central longitudinal axis, and wherein the central longitudinal axis of the proximal bore defines an acute angle with the central longitudinal axis of the proximal bore when viewed in a plane extending in a medial-lateral direction; and
a tapered metaphyseal component having a proximal end and a distal end, an interior surface defining a distal bore at the distal end and an interior surface defining a proximal bore at the proximal end, wherein the distal bore is sized and shaped to be capable of selectively receiving at least a portion of the femoral adapter for selectively mounting the tapered metaphyseal component to the adapter;
wherein the connecting end of the stem extension is sized and shaped to be capable of being selectively connected directly to the proximal tibial component, to the proximal end of the femoral adapter, and to the proximal end of the tapered metaphyseal component.

13. The modular orthopaedic knee implant system of claim 12 wherein the central longitudinal axis of the distal bore of the femoral adapter and the central longitudinal axis of the proximal bore of the femoral adapter are co-linear when viewed in a plane extending in an anterior-posterior direction.

14. The modular orthopaedic knee implant system of claim 12 wherein the central longitudinal axis of the distal bore of the second femoral adapter is offset from and parallel to the central longitudinal axis of the proximal bore of the second femoral adapter when viewed in a plane extending in an anterior-posterior direction.

15. The modular orthopaedic knee implant system of claim 12 further comprising a second femoral adapter having a proximal end, a distal end, an interior surface defining a proximal bore having a central longitudinal axis, an interior surface defining a distal bore having a central longitudinal axis defining an angle with the central longitudinal axis of the proximal bore when viewed in a plane extending in a medial-lateral direction, the angle of the second femoral adapter being different from the angle of the first femoral adapter.

* * * * *